(12) United States Patent
Beaumont et al.

(10) Patent No.: US 10,702,884 B2
(45) Date of Patent: Jul. 7, 2020

(54) VOLATILE MATERIAL DISPENSER WITH NEBULIZER AND NEBULIZER ASSEMBLY

(71) Applicant: S. C. JOHNSON & SON, INC., Racine, WI (US)

(72) Inventors: Dennis J. Beaumont, Libertyville, IL (US); Jesse Richard, Racine, WI (US); Scott D. Walter, Twin Lakes, WI (US); Daniel S. McGrath, Gurnee, IL (US)

(73) Assignee: S. C. Johnson & Son, Inc., Racine, WI (US)

( * ) Notice: Subject to any disclaimer, the term of this patent is extended or adjusted under 35 U.S.C. 154(b) by 276 days.

(21) Appl. No.: 15/308,239

(22) PCT Filed: May 12, 2015

(86) PCT No.: PCT/US2015/030362
§ 371 (c)(1),
(2) Date: Nov. 1, 2016

(87) PCT Pub. No.: WO2015/175527
PCT Pub. Date: Nov. 19, 2015

(65) Prior Publication Data
US 2017/0056914 A1    Mar. 2, 2017

Related U.S. Application Data

(60) Provisional application No. 61/992,027, filed on May 12, 2014.

(51) Int. Cl.
*B05B 17/06* (2006.01)
*A01M 1/20* (2006.01)
(Continued)

(52) U.S. Cl.
CPC .......... *B05B 17/0653* (2013.01); *A01M 1/205* (2013.01); *A01M 1/2033* (2013.01);
(Continued)

(58) Field of Classification Search
CPC ............ B05B 17/0653; B05B 17/0684; A01M 1/2033; A01M 1/205; A61L 9/127; A61L 9/122; A61L 9/14
See application file for complete search history.

(56) References Cited

U.S. PATENT DOCUMENTS

| | | |
|---|---|---|
| 4,605,167 A | 8/1986 | Maehara |
| 4,621,768 A | 11/1986 | Lhoste et al. |

(Continued)

FOREIGN PATENT DOCUMENTS

| | | |
|---|---|---|
| CN | 1296457 A | 5/2001 |
| CN | 1630562 A | 6/2005 |

(Continued)

OTHER PUBLICATIONS

International Search Report and Written Opinion for International Application No. PCT/US2015/030362, dated Feb. 1, 2016.

(Continued)

*Primary Examiner* — Regina M Yoo
(74) *Attorney, Agent, or Firm* — Quarles & Brady LLP

(57) ABSTRACT

A volatile material dispenser may include a housing adapted to hold a refill containing a volatile material and a nebulizer in communication with the refill and the volatile material within the refill, wherein the nebulizer is adapted to volatilize and emit the volatile material as nebulized particles. The nebulizer may include a piezoelectric element having a central aperture and first and second opposing surfaces and an orifice plate disposed adjacent the first surface of the piezoelectric element.

19 Claims, 9 Drawing Sheets

(51) Int. Cl.
*A61L 9/12* (2006.01)
*A61L 9/14* (2006.01)

(52) U.S. Cl.
CPC .............. *A61L 9/122* (2013.01); *A61L 9/127* (2013.01); *A61L 9/14* (2013.01); *B05B 17/0684* (2013.01); *A61L 2209/132* (2013.01); *A61L 2209/133* (2013.01)

(56) References Cited

U.S. PATENT DOCUMENTS

| | | | |
|---|---|---|---|
| 5,518,179 A * | 5/1996 | Humberstone | B05B 17/0646 239/102.2 |
| 6,293,474 B1 * | 9/2001 | Helf | A01M 1/205 239/102.1 |
| 6,296,196 B1 | 10/2001 | Denen et al. | |
| 6,354,513 B1 | 3/2002 | Basaganas Millan | |
| 6,378,780 B1 | 4/2002 | Martens, III et al. | |
| 6,382,522 B2 * | 5/2002 | Tomkins | A01M 1/205 239/102.1 |
| 6,439,474 B2 | 8/2002 | Denen | |
| 6,619,560 B1 | 9/2003 | Chun | |
| 6,843,430 B2 * | 1/2005 | Boticki | B05B 17/0646 239/102.1 |
| 6,969,008 B2 * | 11/2005 | Helf | A47F 7/286 239/4 |
| 7,455,245 B2 | 11/2008 | Sipinski et al. | |
| 7,543,761 B2 * | 6/2009 | Mehus | A61L 9/14 239/10 |
| 8,955,765 B2 | 2/2015 | Porchia et al. | |
| 10,112,203 B2 | 10/2018 | Kubicek et al. | |
| 2003/0206834 A1 | 11/2003 | Chiao et al. | |
| 2003/0218077 A1 * | 11/2003 | Boticki | B05B 17/0646 239/102.1 |
| 2006/0011737 A1 | 1/2006 | Amenos et al. | |
| 2006/0120080 A1 | 6/2006 | Sipinski et al. | |
| 2013/0026250 A1 * | 1/2013 | Burt | A01M 1/205 239/302 |
| 2013/0292484 A1 * | 11/2013 | Jackson | A01M 1/205 239/4 |
| 2013/0334336 A1 * | 12/2013 | Haran | A61L 9/14 239/4 |
| 2013/0334337 A1 * | 12/2013 | Haran | A61L 9/14 239/11 |
| 2014/0367486 A1 * | 12/2014 | Kawano | A61L 9/14 239/102.2 |

FOREIGN PATENT DOCUMENTS

| | | |
|---|---|---|
| CN | 101313177 A | 11/2008 |
| CN | 101432028 A | 5/2009 |
| CN | 102307674 A | 1/2012 |
| JP | 2005526610 A | 9/2005 |
| WO | WO2000053337 | 9/2000 |
| WO | WO2003068413 A1 | 8/2003 |
| WO | 2004008889 A1 | 1/2004 |
| WO | WO2007056147 A1 | 5/2007 |
| WO | WO2008036263 A2 | 3/2008 |
| WO | 2013129120 A1 | 9/2013 |
| WO | WO2013129120 | 9/2013 |
| WO | WO2013146639 A1 | 10/2013 |

OTHER PUBLICATIONS

Notification of Reasons for Refusal issued in corresponding Japanese Patent Application No. 2016-567189, dated Jul. 24, 2018, 8 pages.

Grounds for Rejection, related Chinese application No. 201580025181.6, dated Dec. 4, 2018, 26 pages.

* cited by examiner

VOLATILE MATERIAL DISPENSER WITH NEBULIZER AND NEBULIZER ASSEMBLY

This application represents the U.S. National Stage of International Application No. PCT/US2015/030362, filed May 12, 2015, which is based on, claims priority to, and incorporates herein by reference in its entirety, U.S. Provisional Patent Application Ser. No. 61/992,027, filed May 12, 2014, and entitled, "VOLATILE MATERIAL DISPENSER WITH NEBULIZER AND NEBULIZER ASSEMBLY."

BACKGROUND

1. Field of the Disclosure

The present invention relates generally to volatile material dispensers and, more particularly, to volatile material dispensers that dispense volatile materials with a nebulizer.

2. Description of the Background

Various volatile material dispensers are known in the prior art, most of which deliver fragrance to the air by a number of different mechanisms, including, for example: (1) the fragrance is sprayed into the air or (2) the fragrance is evaporated into the air. Such volatile material dispensers generally include a housing with a refill inserted therein. The refill generally includes a container for holding a volatile material, wherein the volatile material may include various components including aroma chemicals, water, solvents, surfactants, alcohols, and other components. Some refills include a wick in contact with the volatile material and extending out of the refill to carry the volatile material out of the refill. Other refills include a gel-like substance that is emitted through a semi-permeable membrane. Regardless of the type of refill, a refill may be inserted into a volatile material dispenser having a heater, a piezoelectric element, an aerosol actuator, or any other diffusion element that may assist in delivering the volatile material.

SUMMARY

According to one illustrative embodiment, a volatile material dispenser may comprise a housing adapted to hold a refill containing a volatile material and a nebulizer in communication with the refill and the volatile material within the refill, wherein the nebulizer is adapted to volatilize and emit the volatile material as nebulized particles. The nebulizer may include a piezoelectric element having a central aperture and first and second opposing surfaces, an orifice plate disposed adjacent the first surface of the piezoelectric element and extending into the central aperture and beyond the second surface of the piezoelectric element, and a plate disposed adjacent the orifice plate opposite the piezoelectric element.

In illustrative embodiments, a first side of the nebulizer may be positioned adjacent an absorbent member by a spring and the absorbent member may be adapted to contact a wick of a refill when a refill is inserted within the housing.

In illustrative embodiments, the volatile material dispenser may include a refill that may comprise a body, a neck extending outwardly from the body and providing an opening into the body, and a wick disposed within the body and having an end extending out the neck. The refill may further include an absorbent member disposed in contact with the end of the wick, a retaining member disposed within the neck for holding the wick in position, and a barb extending inwardly from the retaining member for preventing axial movement of the wick within the neck of the refill.

In illustrative embodiments, the absorbent member may be selected from the group consisting of a felt pad and cotton wool.

In illustrative embodiments, the volatile material dispenser may further include a refill disposed within the housing, wherein the refill may include a volatile material comprised of at least about 50% by weight water. In illustrative embodiments, the refill may include a volatile material comprised of between about 60% by weight and about 80% by weight water, at least one solvent, and at least on fragrance component.

In illustrative embodiments, the volatile material dispenser may include a fan disposed within the housing for moving air from a lower portion of the housing and around the nebulizer and out a top portion of the housing In illustrative embodiments, the plate may be made of stainless steel and may include a disc-shaped portion with a central hole and a cylindrical portion surrounding the central hole and extending toward the piezoelectric element According to another illustrative embodiment, a volatile material dispenser may include a housing adapted to hold a refill containing a volatile material and a nebulizer in communication with the refill and the volatile material within the refill, wherein the nebulizer is adapted to volatilize and emit the volatile material as nebulized particles. The nebulizer may include a piezoelectric element having a central aperture and first and second opposing surfaces and an orifice plate disposed adjacent the first surface of the piezoelectric element.

In illustrative embodiments, the volatile material dispenser may further include a cavity disposed within the housing and formed by at least first and second opposing walls. An absorbent member may be positioned adjacent the first wall forming the cavity and the nebulizer may be positioned adjacent the absorbent member by a spring that extends between the nebulizer and the second wall forming the cavity.

In illustrative embodiments, the orifice plate extends into the central aperture of the piezoelectric element and beyond the second surface of the piezoelectric element.

In illustrative embodiments, the refill may include a body, a neck extending outwardly from the body and providing an opening into the body, a wick disposed within the body and having an end extending out the neck, and an absorbent member disposed in contact with the end of the wick, wherein, when the refill is inserted into the housing of the volatile material dispenser, the absorbent member contacts the nebulizer.

In illustrative embodiments, the absorbent member may be selected from the group consisting of a felt pad and cotton wool.

In illustrative embodiments, the volatile material dispenser may include a fan disposed within the housing for moving air from a lower portion of the housing and around the nebulizer and out a top portion of the housing.

In illustrative embodiments, the nebulizer may further include a stainless steel plate disposed between the spring and the orifice plate, wherein the stainless steel plate may include a disc-shaped portion with a central hole and a cylindrical portion surrounding the central hole and extending toward the piezoelectric element.

In illustrative embodiments, the volatile material dispenser may further include a refill disposed within the housing, wherein the refill may include a volatile material comprised of at least about 50% by weight water. In illustrative embodiments, the refill may include a volatile material comprised of between about 60% by weight and about 80% by weight water, at least one solvent, and at least on fragrance component.

According to a further illustrative embodiment, a nebulizer assembly may include a piezoelectric element having a central aperture and first and second opposing surfaces and an orifice plate disposed adjacent the first surface and extending into the central aperture and beyond the second surface of the piezoelectric element. The nebulizer assembly may further include a stainless steel plate disposed adjacent the orifice plate opposite the piezoelectric element.

In illustrative embodiments, in use, the nebulizer assembly may be disposed within a cavity formed by first and second opposing walls, an absorbent member is positioned adjacent the first wall, and the nebulizer assembly is positioned adjacent the absorbent member between the absorbent member and the second wall.

In illustrative embodiments, the absorbent member may be a component of the nebulizer assembly.

In illustrative embodiments, the absorbent member is connected to a wick of a refill that has been placed in communication with the nebulizer assembly.

In illustrative embodiments, wherein the absorbent member may be selected from the group consisting of a felt pad and cotton wool.

BRIEF DESCRIPTION OF THE DRAWINGS

Other aspects and advantages of the present invention will become apparent upon consideration of the following detailed description, wherein similar structures have like or similar reference numerals.

DETAILED DESCRIPTION

The present disclosure is directed to volatile material dispensers and methods of emitting volatile materials therefrom. While the present disclosure may be embodied in many different forms, several specific embodiments are discussed herein with the understanding that the present disclosure is to be considered only as an exemplification of the principles of the disclosure, and it is not intended to limit the disclosure to the embodiments illustrated.

Figure 1:
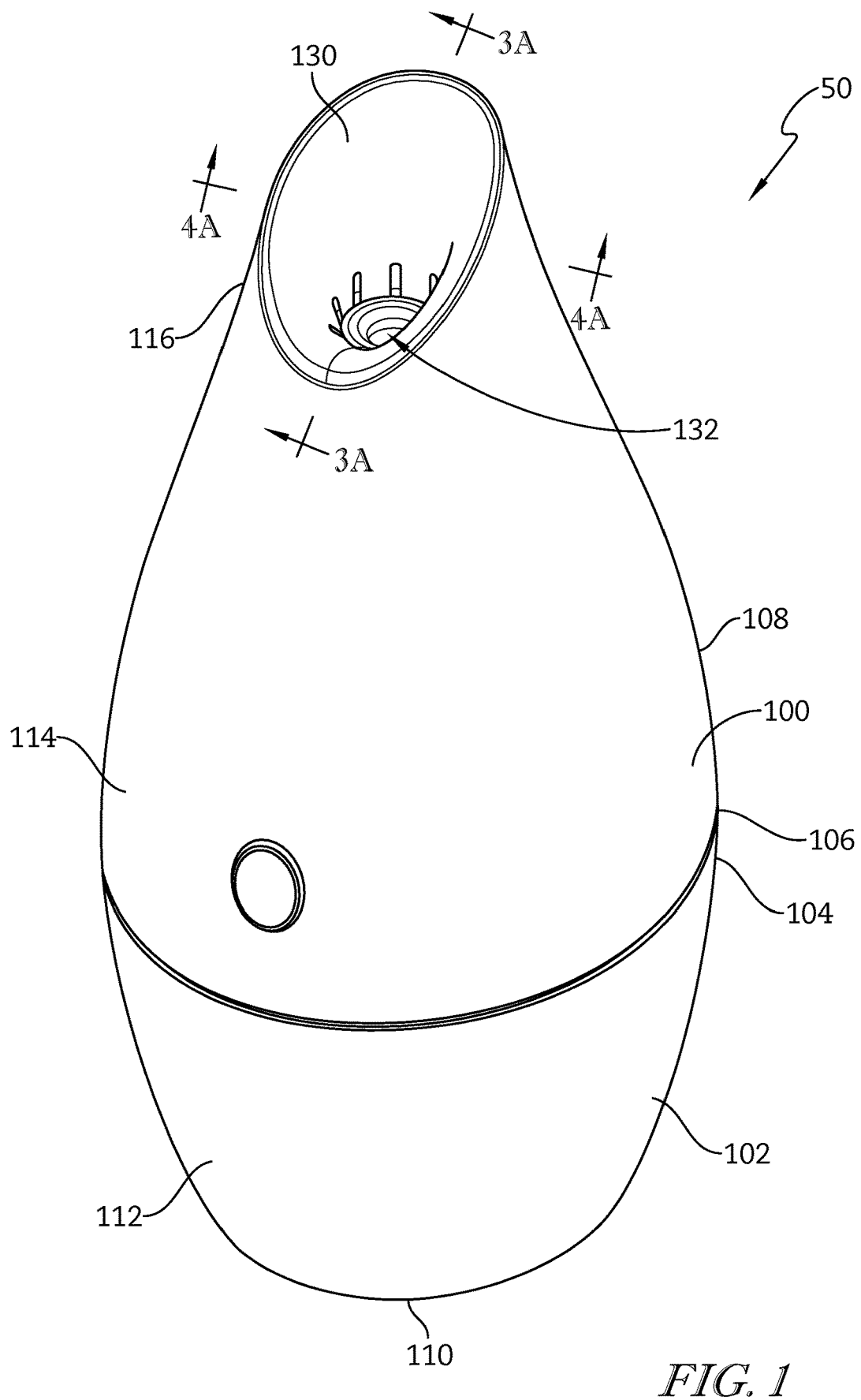
FIG. 1 top and front perspective view of an embodiment of a volatile material dispenser.
Figure 2:
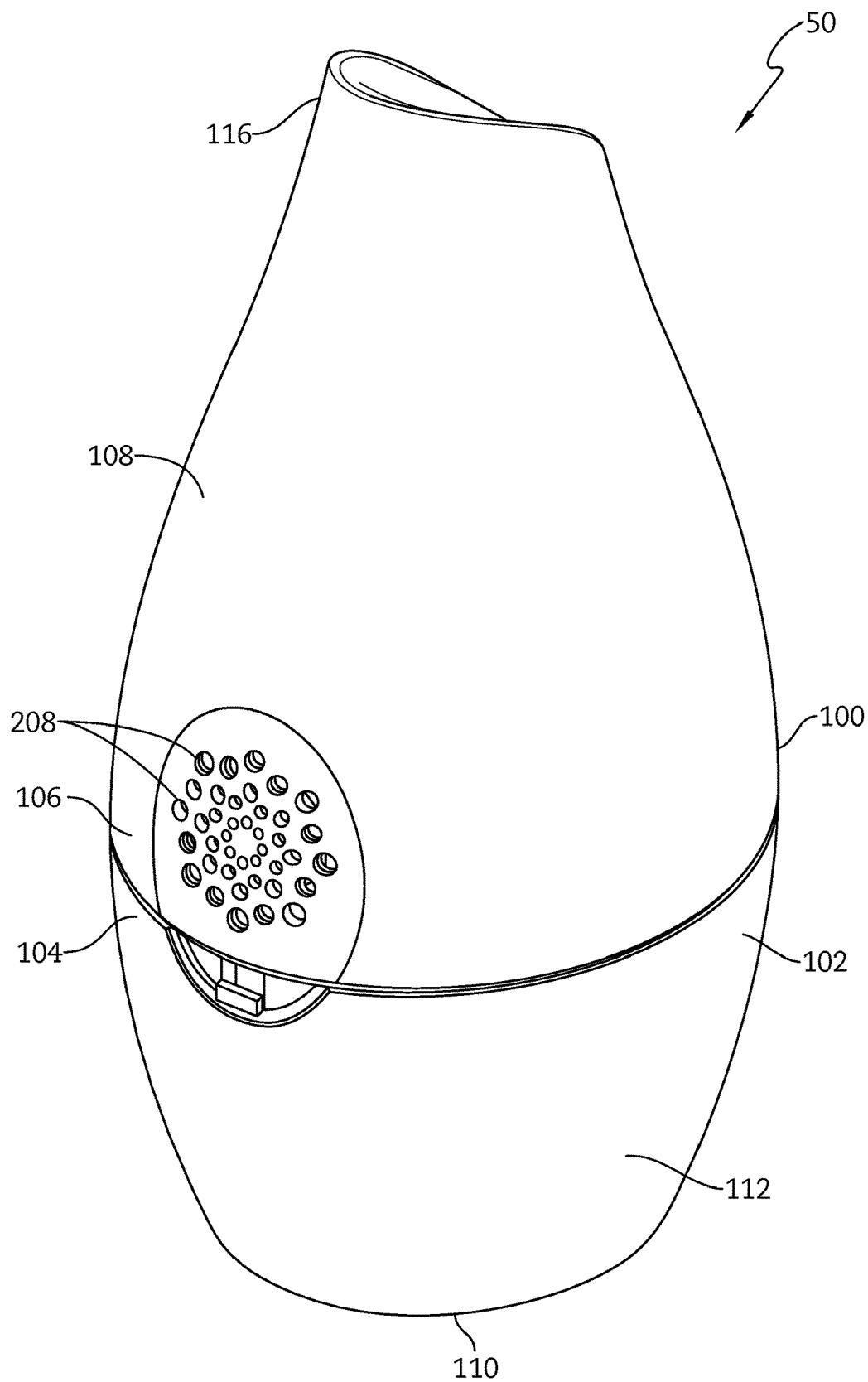
FIG. 2 is a top and rear perspective view of the volatile material dispenser of FIG. 1.
Figure 6:
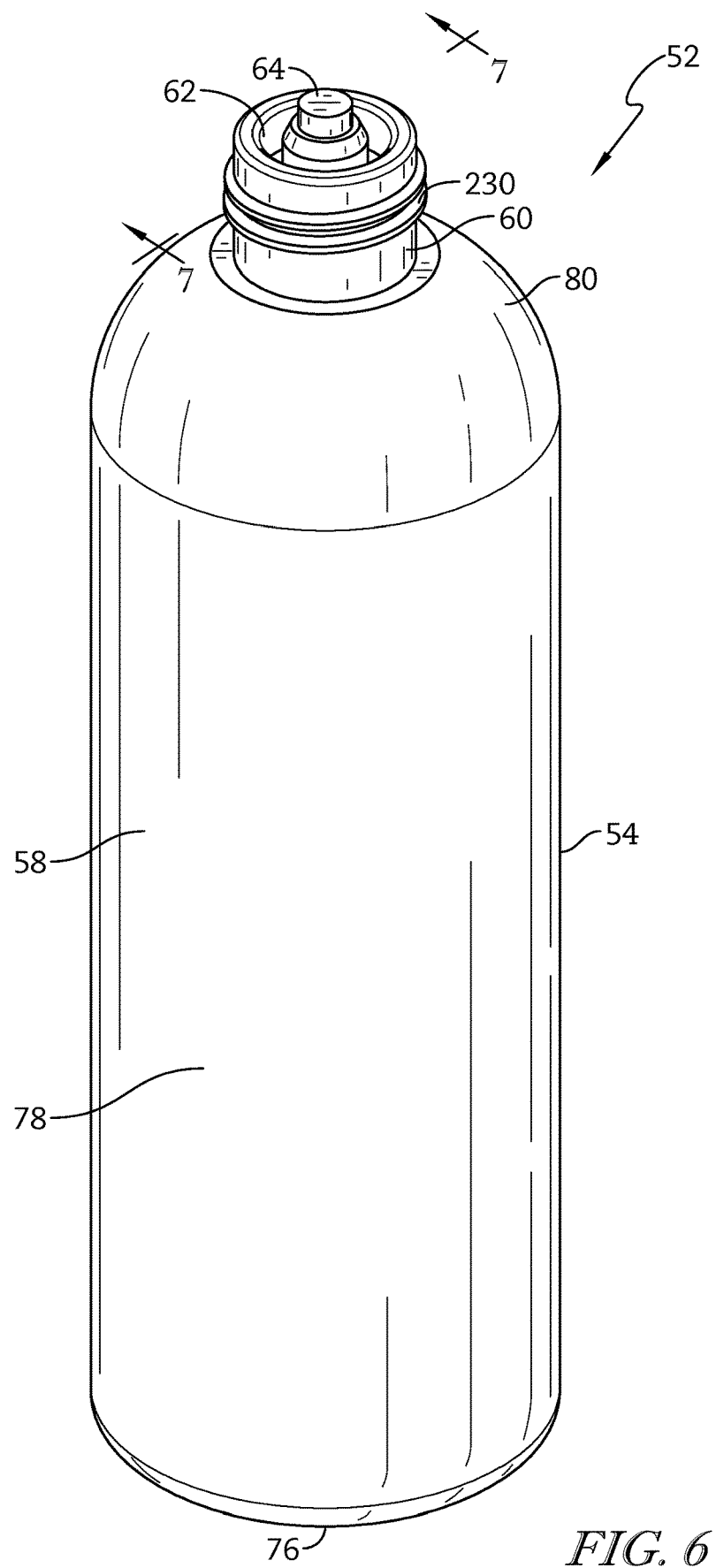
FIG. 6 is a top perspective view of a refill containing a mixture of at least water and fragranced oil, wherein the refill is adapted for insertion into the volatile material dispenser of FIGS. 1-4B.
Figure 7:
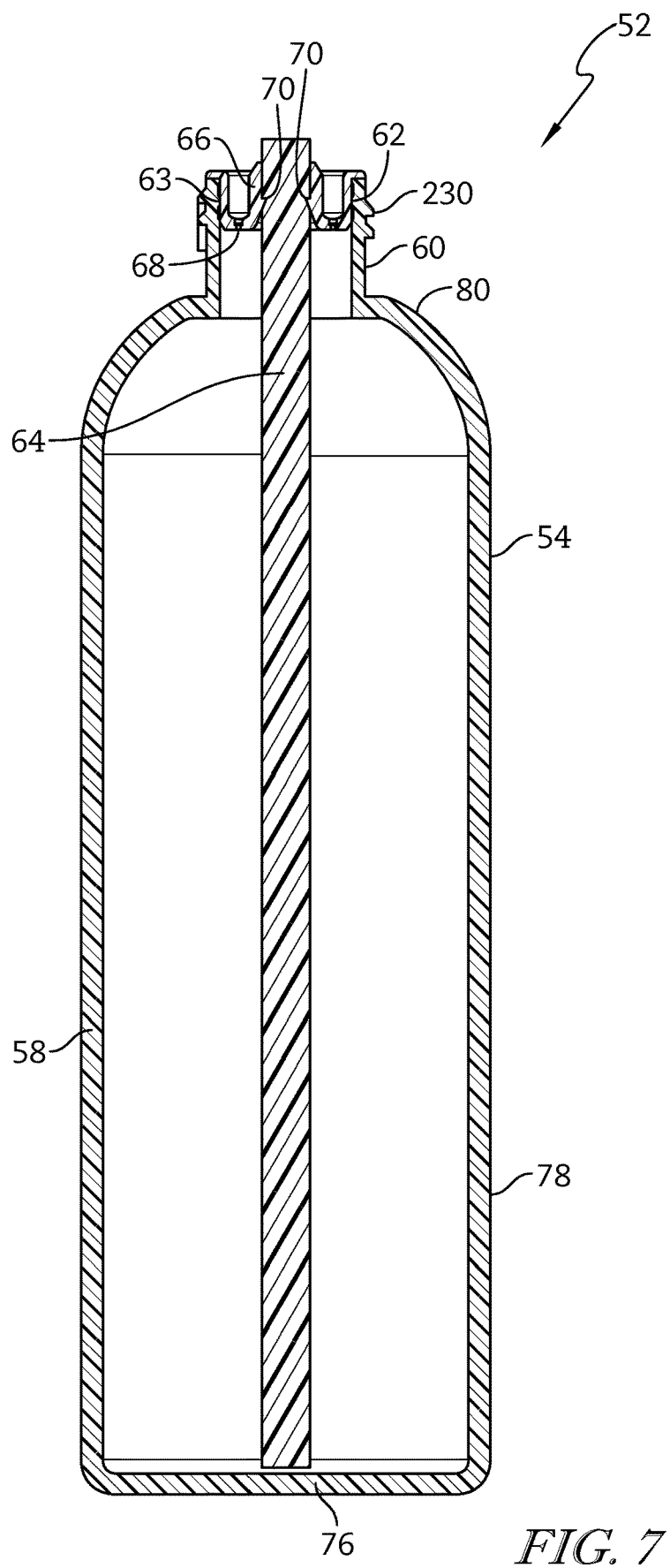
FIG. 7 is a cross-sectional view taken generally along the lines 7-7 of FIG. 6.

Referring to the drawings, FIGS. 1 and 2 depict a volatile material dispenser 50. The dispenser 50 may be adapted to accommodate a refill 52 (FIGS. 3A-4B, 6, and 7) and dispense a volatile material in the form of water and/or fragranced oil from the refill. The refill 52, as seen in FIGS. 6 and 7, generally includes a container 54 for holding the volatile material therein, wherein the container 54 is adapted to be retained within the dispenser 50. The container 54 includes a body 58 for holding the volatile material and a neck 60 extending outwardly from the body 58 and providing an opening into the container 54. A retaining mechanism 62 is disposed within the neck 60 for holding a wick 64 with a first end of the wick 64 in contact with the volatile material and a second end of the wick 64 extending out of the container 54 through the neck 60. In illustrative embodiments, the wick 64 may be formed of extruded fibers that are bundled together into the shape of a rod. In alternative illustrative embodiments, the wick 64 may be formed of rope or one or more cotton cords. Optionally, the wick 64 may be formed in any suitable shape or of any suitable material. The retaining mechanism 62 is retained within the neck 60 of the refill 52 by an interference fit, a friction fit, or in any other suitable manner that holds the retaining mechanism 62 in place within the neck 60. As best seen in FIG. 6, the retaining mechanism 62 may include an outer cylindrical wall 63 and an inner cylindrical wall 66 joined by a connecting member 68. As best seen in FIGS. 3B, 4B, and 6, a single circumferential or a plurality of discrete barbs 70 may extend from an inner surface 72 of the inner cylindrical wall 66 to retain the wick 64 in position within the retaining mechanism 62 and, thus, within the refill 52. The body 58 of the refill 52 includes a generally flat base portion 76 and a cylindrical side wall 78 extending upwardly from the base portion 76, and a curved top wall 80 that joins the sidewall 66 to the neck 60.

Although a refill 52 is shown and described with particularity, it is contemplated that any type of refill may be used with variations of the dispensers described herein. For example, a refill with a flexible container may be utilized. Still further, the delivery system (i.e., the wick) may be different and/or the size and/or the shape of the container may be different.

The volatile material disposed in the container 54 may include water, solvents, and one or more fragranced oil components. The volatile material may additional include one or more other active ingredients, for example, a cleaner, an insecticide, an insect repellant, an insect attractant, a disinfectant, a mold or mildew inhibitor, a disinfectant, an air purifier, an aromatherapy scent, an antiseptic, an odor eliminator, a positive fragrancing volatile material, an air-freshener, a deodorizer, or the like, and combinations thereof. Additives may additionally be included in the volatile material, such as, for example, preservatives.

The volatile material within the container 54 preferably includes at least 50% by weight water or between about 50% by weight and about 80% by weight water. The volatile material more preferably includes between about 60% by weight and about 75% weight water. The volatile material most preferably includes between about 65% by weight and about 70% by weight water.

In illustrative embodiments, the volatile material may include between about 0.01% by weight and about 10% by weight fragrance components. In other illustrative embodiments, the volatile material may include between about 1% by weight and about 3% by weight fragrance components or between about 5% by weight and about 8% by weight fragrance components. In illustrative embodiments, the volatile material may be free of surfactants.

Referring to FIGS. 1-4B, the dispenser 50 includes a housing 100 that includes a lower housing portion 102 attached at an upper end 104 to a lower end 106 of an upper housing portion 108. The lower housing portion 102 is formed by a bottom wall 110 and a first side wall 112 with a circular cross-section that increases between the bottom wall 110 and the upper end 104. Similarly, the upper housing portion 106 is formed of a second side wall 114 that decreases in cross-section between the lower end 106 and a top edge 116 of the upper housing portion 106. As best seen in FIGS. 1 and 3A-4B, the upper housing portion 108 further includes a curved wall 120 that extends from the top edge 116 to create a cavity 122 within the upper housing portion 108. As best seen in FIGS. 3A-4B, an outlet manifold 130 is attached to the upper housing portion 108 within the cavity 122 by a snap fit, adhesive, friction fit, interference fit, or in any other suitable manner. The outlet manifold 130 mimics a shape of the curved wall 120 and provides an outlet channel 132 for volatilized volatile material. In illustrative embodiments, the outlet manifold 130 may be removable, for example, for cleaning and/or replacement.

Referring to FIGS. 3A-4B, the housing 100 encloses the refill 52 and electronic components of the dispenser 50. A support 150 is positioned between the lower and upper housing portions 102, 108 and assists in supporting a number of electrical components of the dispenser 50. In illustrative embodiments, the support 150 may be attached to or integrally formed as part of the lower or upper housing portions 102, 108. In illustrative embodiments, the support 150 may be attached to or integrally formed as part of the upper housing portion 108 such that the lower housing portion 102 may be removed, for example, to enable replacement of the refill 52.

Figure 3A:
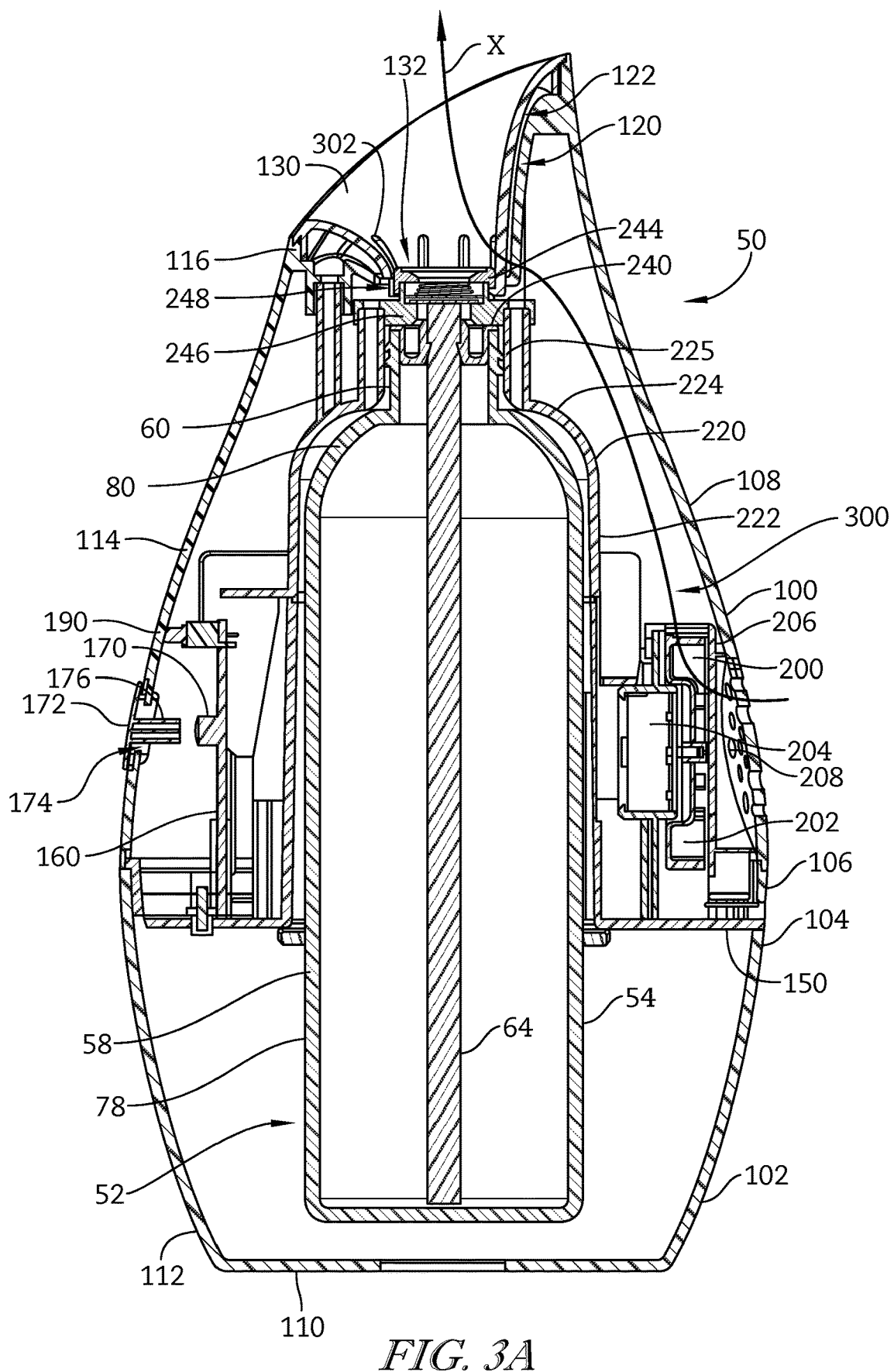
FIG. 3A is a cross-sectional view of the volatile material dispenser of FIGS. 1 and 2 taken generally along the lines 3A-3A of FIG. 1.
Figure 3B:
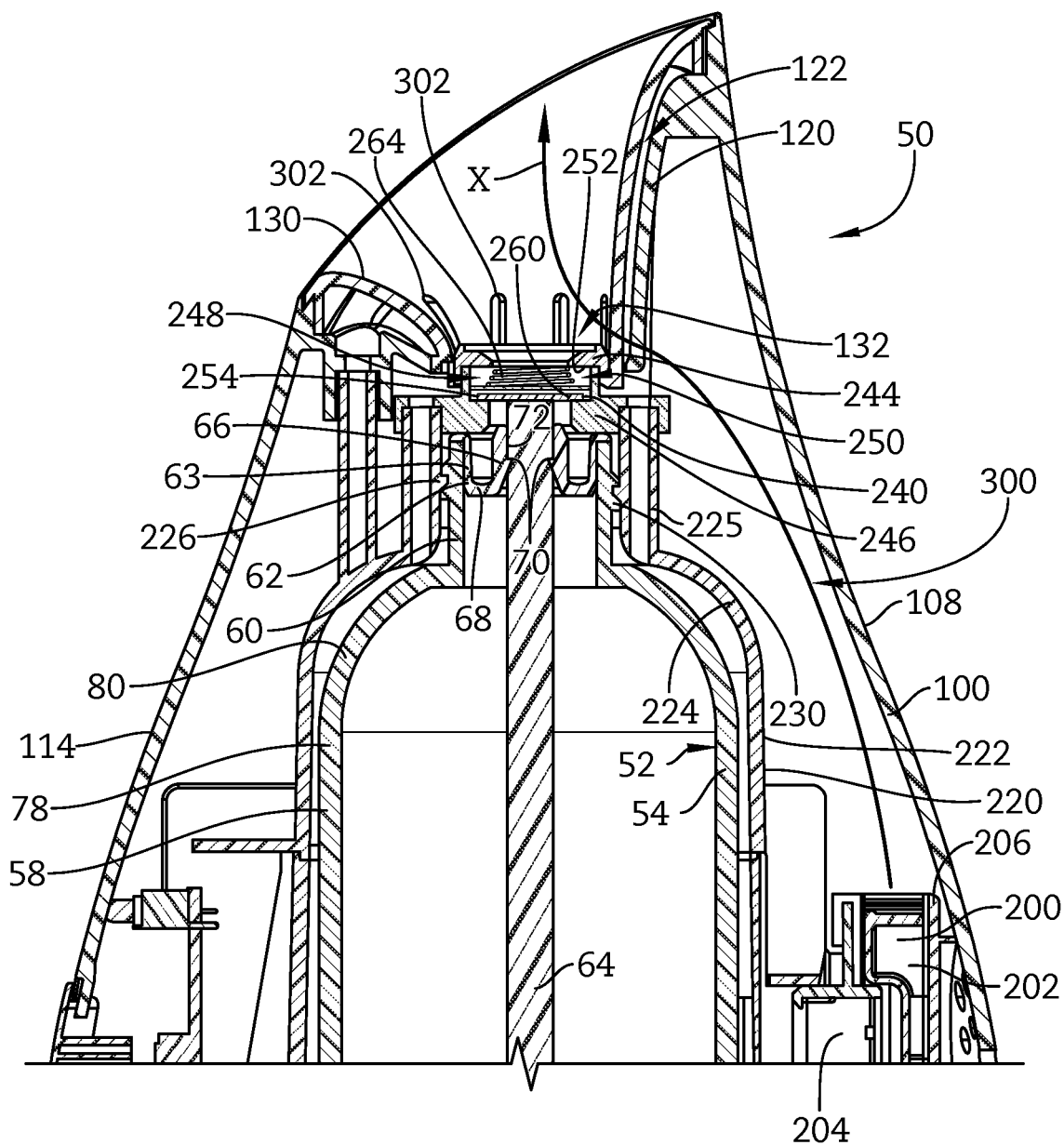
FIG. 3B is an enlarged section of FIG. 3A depicting a nebulizer of the volatile material dispenser of FIGS. 1 and 2.

As best seen in FIG. 3A, a printed circuit board (PCB) 160 or other control circuitry is supported by the support 150. A number of batteries 161, for example, four batteries, may be enclosed within a casing 162 and may be electrically connected to the PCB 160 for providing electrical power to the PCB 160 other electrical components of the dispenser 50, as will be discussed below. Optionally or additionally, the dispenser 50 may be provided with a universal serial bus (USB) port, electrical prongs, a cord, or any other suitable electrical connector to provide electrical power to the dispenser 50.

A switch 170 extends from the PCB 160, wherein activation of the switch 170 may turn the dispenser 50 on and off. In particular, a button 172 may extend through a hole 174 within the housing 100 such that the button 172 is accessible to a user of the dispenser 50. An actuator arm 176 extends from a rear side of the button 172 and is spaced from the switch 170. When a user presses a front side of the button 172, the actuator arm 176 depresses the switch 170 to turn the device on or off. Optionally, the switch 170 may operate to alter any function of the dispenser 50, for example, an air flow generator speed, a volatile material emission rate, boost of fragrance, or another other suitable function. Still further, the dispenser 50 may include any number of switches that operate any number of different functions of the dispenser 50. In an illustrative embodiment, the dispenser 50 includes an automatic shut-off function that deactivates the dispenser 50 after a particular period of time, for example, 3 hours.

The dispenser 50 may also include one or more light emitting diodes (LEDs) 190 either extending from the PCB 160 or positioned in any suitable location within the dispenser 50. The one or more LEDs 190 may indicate that the dispenser 50 is on or off, may provide an alert, and/or may provide any other suitable indicator for a user. The LEDs 190 may extend through an aperture in the housing 100 or may be positioned behind the housing 100 to allow the LEDs 190 to shine through the housing 100.

Referring again to FIG. 3A, an air flow generator 200 may also be supported by the support 150 and electrically connected to the PCB 160 such that the PCB 160 may control operation of the air flow generator 200. The air flow generator 200 generally includes a plurality of blades 202 that are rotated by a motor 204. An air flow generator housing 206 may encase and prevent access to the air flow generator 200. The air flow generator 200 may operate continuously, intermittently, or may operate according to one or more pre-defined programs implemented within the PCB 160. The air flow generator 200 pulls air through apertures 208 in the upper housing portion 108 for movement through the housing 100, as will be discussed in greater detail hereinbelow. The air flow generator 200 may be, for example, a blower, a fan, and/or any other suitable device(s) for creating a flow of air.

Figure 4A:
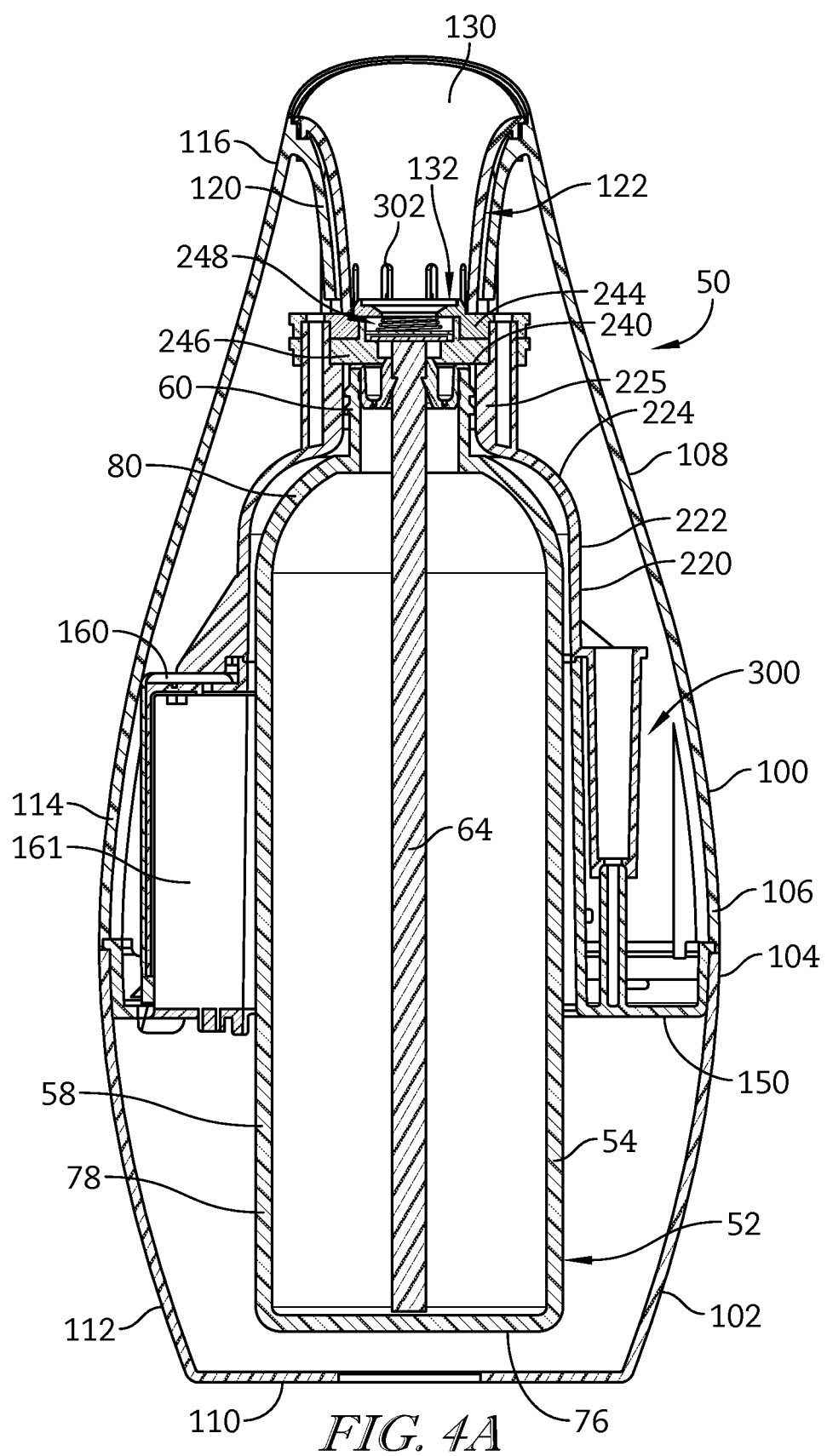
FIG. 4A is cross-sectional view of the volatile material dispenser of FIGS. 1 and 2 taken generally along the lines 4A-4A of FIG. 1.
Figure 4B:
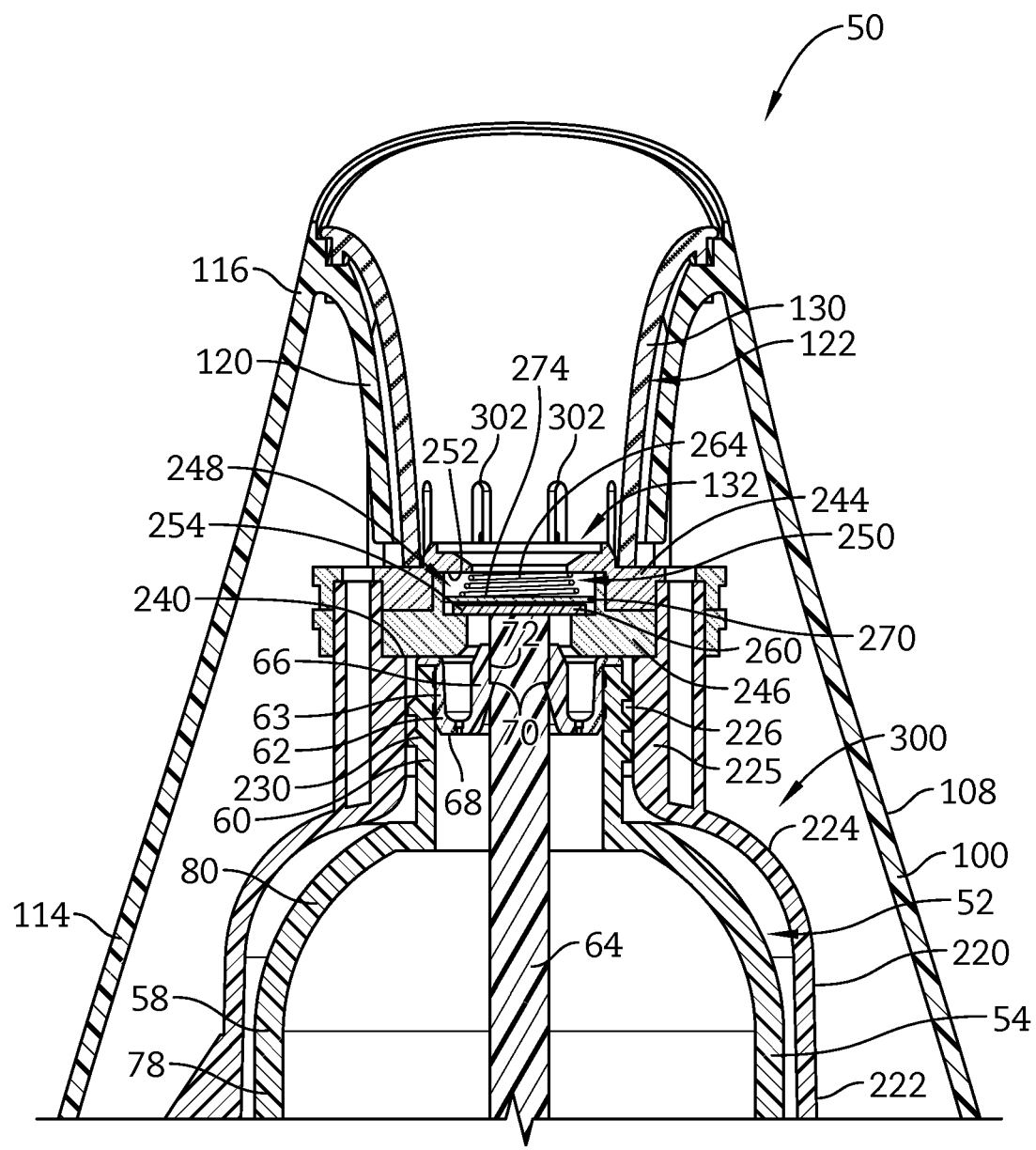
FIG. 4B is an enlarged section of FIG. 4A depicting the nebulizer of the volatile material dispenser of FIGS. 1 and 2.

A chassis 220, as best seen in FIGS. 3A and 4A, may be attached to or integral with the support 150 to retain in position other components of the dispenser 50. The chassis 220 may have a cylindrical wall 222 that extends upwardly from the support 150 and a curved wall 224 that extends from the cylindrical wall 222 and terminates at a cylindrical wall 225 that may have threads 226 for attachment of the refill 52. In illustrative embodiments, threads 230 may be disposed on the neck 60 of the refill 52 for mating with the threads 226 of the vertical wall 224 to attach the refill 52 to the chassis 220. In other illustrative embodiments, the refill 52 may be attached to the chassis 220 in any other suitable manner.

Referring to FIGS. 3A-4B, the vertical wall 224 may include a ledge 240 for holding top and bottom shells 244, 246 for supporting a nebulizer assembly 248. More particularly, a cavity 250 may be formed between an inner surface 252 of the top shell 244 and an inner surface 254 of the bottom shell 246, wherein the nebulizer assembly 248 is positioned within the cavity 250. The nebulizer assembly 248 includes an absorbent material 260 positioned adjacent the inner surface 254 of the bottom shell 246, a nebulizer 262 disposed adjacent the absorbent material 260, and a spring 264 may be positioned between the nebulizer 262 and the inner surface 252 of the top shell 244. The spring 264, if present, retains the absorbent material 260 in position adjacent the inner surface 254 of the bottom shell 246 and the nebulizer 262 in position adjacent the absorbent material 260. While a spring 264 is depicted in the figures, the nebulizer assembly 248 may not include a spring 264.

In illustrative embodiments, the absorbent material 260 may be a felt pad and/or cotton wool. In other illustrative embodiments, the absorbent material 260 may be formed of a felt pad, a velour pad, cotton wool, cotton cloth, chenille yarn, chenille fabric, polyester cloth, paper towel, synthetic cloth, synthetic nonwoven material, a cotton ball or swab, combinations thereof, or other suitable absorbent material (s). The absorbent material 260 may be a component of the nebulizer assembly 248 or may be attached or otherwise in communication with the wick 64 of the refill 52.

Figure 5:
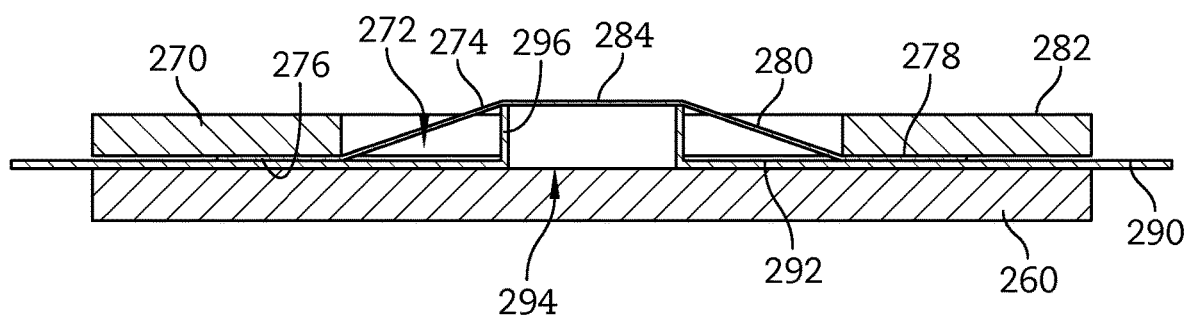
FIG. 5 is a cross-sectional view of the nebulizer of FIGS. 3A-4B.

As best seen in FIG. 5, the nebulizer 262 includes a piezoelectric element 270, which, in use, is positioned adjacent the absorbent material 260. In illustrative embodiments, the piezoelectric element 270 may be formed as a ring with a central aperture 272 and may be made of ceramic. In alternative illustrative embodiments, the piezoelectric element 270 may be formed in any suitable shape and/or may be made of any suitable material having piezoelectric properties and which causes the material to change dimensionally in response to an applied electric field. Illustrative examples of suitable materials include, but are not limited to, lead zirconate titanate (PZT) or lead metaniobate (PN).

While a particular piezoelectric element is described, any actuator may be utilized, for example, a piezoelectric vibrating mesh actuator, a piezoelectric standing wave actuator, a piezoelectric vibrating needle, or any other suitable piezoelectric actuator.

Still referring to FIG. 5, an orifice plate 274 may be positioned to extend across the central aperture 272 on a lower surface 276 of the piezoelectric element 270. The orifice plate 274 includes a ring-shaped section 278 that is in contact with the lower surface 276 of the piezoelectric element 270, an angled section 280 that extends from the ring-shaped section 278 to a point above an upper surface 282 of the piezoelectric element 270, and a central apertured section 284 that connects the angled section 280 and provides a plurality of orifices (not shown). In an illustrative embodiment, the orifice plate 274 includes a plurality of orifices having a diameter of between about 3 microns and about 9 microns. In other illustrative embodiments, the orifice plate 274 includes a plurality of orifices having a diameter of between about 3 microns and about 5 microns. In illustrative embodiments, the orifice plate 274 includes between about 250 and about 1000 orifices. In illustrative embodiments, the orifice plate 274 is formed of a polyamide film.

A stainless steel plate 290 may be disposed adjacent the ring-shaped section 276 of the orifice plate 274 to contain the orifice plate 274 between the stainless steel plate 290 and the piezoelectric element 270. In illustrative embodiments, the stainless steel plate 290 includes a ring-shaped section 292 forming a central hole 294 and a cylindrical portion 296 extending upwardly from the ring-shaped section 292 and through the central aperture 272 of the piezoelectric element 270 and surrounding the central hole 294. The cylindrical portion 296 provides an appropriate stiffness for the stainless steel plate 290 for a mechanical resonance that matches an electrical resonance to efficiently create nebulize particles.

Once assembled, as noted above, the nebulizer 262 is positioned with the stainless steel plate 290 adjacent the absorbent material 260, as seen in FIG. 5. The wick 64 of the refill 52 is in direct contact with the absorbent material 260, which provides volatile material from the refill 52 directly to the absorbent material 260 and, therefore, directly to the central apertured section 284 of the orifice plate 274. In alternative illustrative embodiments, the absorbent material 260 is attached to or integral with the wick 64 and provided as part of the refill 52 such that, upon insertion of the refill 52 into the dispenser 50, the absorbent material 260 is in contact with the stainless steel plate 290.

During operation of the nebulizer 262, it is desirable to have the wick 64 in contact with the orifice plate 274. If the wick 64 is not in contact with the orifice plate 274, especially in a water-based fragranced volatile material, the nebulizer 262 may not function properly and/or may not emit volatile material at all. Due to tolerances in the system, for example with a positioning or a length of the wick 64, the wick 64 may not always be in contact with the orifice plate 274. The absorbent material 260, which is flexible, closes any gaps between the wick 64 and the orifice plate 274 as a result of these tolerances. If the wick 64 would have been in contact with the orifice plate 274 regardless of the inclusion of the absorbent material 260, the absorbent material 260 is compressed by the wick 64.

During operation, the nebulizer 262 is actuated, either continuously or intermittently, to dispense volatile material. More particularly, an oscillating electric field is applied to the piezoelectric element 270, which causes expansion and contraction of the piezoelectric element 270 in a radial direction. The expansion and contraction causes the orifice plate 274 to vibrate in an axial direction (along a longitudinal axis of the dispenser 50), forcing volatile material retained within the orifices of the orifice plate 274 away from the nebulizer 262 and into the outlet manifold 130. The air flow generator 200 may also be actuated, either continuously or intermittently, the actuation of which may be coordinated in any suitable manner with operation of the nebulizer 262. As best seen in FIGS. 3A-4B, the air flow generator 200 pulls air in through the apertures 208 in the housing 100 and through a cavity 300 formed between the second side wall 114 of the upper housing portion 108 and the cylindrical wall 222 of the chassis 220. The air travels through the cavity 300, as shown by the arrow X in FIGS. 3A and 3B and through apertures (not shown) formed in the curved wall 120 of the housing 110 and out slots 302 formed in the outlet manifold 130. As the air moves out the slots 302, the moving air pushes volatile material that has been emitted from the nebulizer 262 through the outlet channel 132 and outlet manifold 130 and away from the dispenser 50.

Any of the embodiments described herein may be modified to include any of the structures or methodologies disclosed in connection with other embodiments.

Further, although directional terminology, such as front, back, upper, lower, vertical, horizontal, etc. may be used throughout the present specification, it should be understood that such terms are not limiting and are only utilized herein to convey the orientation of different elements with respect to one another.

All documents cited in the Detailed Description of the Invention are, in relevant part, incorporated herein by reference; the citation of any document is not to be construed as an admission that it is prior art with respect to the present invention.

INDUSTRIAL APPLICABILITY

The present invention provides volatile material dispensers and methods of dispensing volatile materials using a nebulizer. In illustrative embodiments, the nebulizer includes components that retain the nebulizer in fluidic contact with the wick of a refill.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:
1. A nebulizer assembly comprising:
a piezoelectric element having a central aperture and first and second opposing surfaces;
an orifice plate disposed adjacent the first surface and extending into the central aperture and beyond the second surface of the piezoelectric element; and a stainless steel plate disposed adjacent the orifice plate opposite the piezoelectric element,
wherein the stainless steel plate includes a cylindrical portion extending through the central aperture.

2. The nebulizer assembly of claim 1, wherein, in use, the piezoelectric element, the orifice plate, and the stainless steel plate are disposed within a cavity formed by first and second opposing walls, an absorbent member is positioned adjacent the first wall, the stainless steel plate is positioned adjacent the absorbent member, and the piezoelectric element, the orifice plate, and the stainless steel plate are positioned between the absorbent member and the second wall.

3. The nebulizer assembly of claim 2, wherein the absorbent member is a component of the nebulizer assembly.

4. The nebulizer assembly of claim 2, wherein the absorbent member is connected to a wick of a refill that has been placed in communication with the nebulizer assembly.

5. The nebulizer assembly of claim 2, wherein the absorbent member is selected from the group consisting of a felt pad and cotton wool.

6. A volatile material dispenser, comprising:
a housing adapted to hold a refill containing a volatile material; and
a nebulizer in communication with the refill and the volatile material within the refill, wherein the nebulizer is adapted to volatilize and emit the volatile material as nebulized particles and the nebulizer comprises:
a piezoelectric element having a central aperture and first and second opposing surfaces;
an orifice plate disposed adjacent the first surface and extending into the central aperture and beyond the second surface of the piezoelectric element; and
a plate disposed adjacent the orifice plate opposite the piezoelectric element and extending through the central aperture.

7. The volatile material dispenser of claim 6, wherein a first side of the nebulizer is positioned adjacent an absorbent member by a spring and the absorbent member is adapted to contact a wick of a refill when a refill is inserted within the housing.

8. The volatile material dispenser of claim 7, wherein the absorbent member is selected from the group consisting of a felt pad and cotton wool.

9. The volatile material dispenser of claim 6, further including a refill that comprises:
a body;
a neck extending outwardly from the body and providing an opening into the body;
a wick disposed within the body and having an end extending out the neck;
an absorbent member disposed in contact with the end of the wick;
a retaining member disposed within the neck for holding the wick in position; and
a barb extending inwardly from the retaining member for preventing axial movement of the wick within the neck of the refill.

10. The volatile material dispenser of claim 6 further including the refill containing the volatile material, wherein the volatile material is comprised of between about 60% by weight and about 80% by weight water, at least one solvent, and at least one fragrance component.

11. The volatile material dispenser of claim 6, further including a fan disposed within the housing for moving air from a lower portion of the housing and around the nebulizer and out a top portion of the housing.

12. The volatile material dispenser of claim 6, wherein the plate is made of stainless steel and includes a disc-shaped portion with a central hole and a cylindrical portion surrounding the central hole and extending toward the piezoelectric element.

13. A volatile material dispenser, comprising:
a housing adapted to hold a refill containing a volatile material; and
a nebulizer in communication with the refill and the volatile material within the refill, wherein the nebulizer is adapted to volatilize and emit the volatile material as nebulized particles and the nebulizer comprises:
a piezoelectric element having a central aperture and first and second opposing surfaces;
an orifice plate disposed adjacent the first surface of the piezoelectric element; and
a plate disposed in contact with the orifice plate opposite the piezoelectric element, and wherein a disc-shaped portion of the plate extends to a position below the central aperture,
wherein the plate is a stainless steel plate, and the plate includes the disc-shaped portion with a central hole and a cylindrical portion surrounding the central hole and extending through the piezoelectric element.

14. The volatile material dispenser of claim 13, further including:
a cavity disposed within the housing and formed by at least first and second opposing walls, wherein an absorbent member is positioned adjacent the first wall forming the cavity, the nebulizer is positioned adjacent the absorbent member by a spring that extends between the nebulizer and the second wall forming the cavity.

15. The volatile material dispenser of claim 13, wherein the orifice plate extends into the central aperture and beyond the second surface of the piezoelectric element.

16. The volatile material dispenser of claim 13, further including a refill that comprises:
a body;
a neck extending outwardly from the body and providing an opening into the body;
a wick disposed within the body and having an end extending out the neck; and
an absorbent member disposed in contact with the end of the wick;
wherein, when the refill is inserted into the housing of the volatile material dispenser, the absorbent member contacts the nebulizer.

17. The volatile material dispenser of claim 16, wherein the absorbent member is selected from the group consisting of a felt pad and cotton wool.

18. The volatile material dispenser of claim 13, further including a fan disposed within the housing for moving air from a lower portion of the housing and around the nebulizer and out a top portion of the housing.

19. The volatile material dispenser of claim 13 further including the refill containing the volatile material, wherein the volatile material is comprised of between about 60% by weight and about 80% by weight water, at least one solvent, and at least one fragrance component.

* * * * *